US008781632B2

(12) United States Patent
Tohidi et al.

(10) Patent No.: US 8,781,632 B2
(45) Date of Patent: Jul. 15, 2014

(54) HYDRATE MONITORING SYSTEM

(75) Inventors: Bahman Tohidi, Edinburgh (GB); Jinhai Yang, Edinburgh (GB); Antonin Chapoy, Bo'ness (GB)

(73) Assignee: Heriot-Watt University, Edinburgh (GB)

(*) Notice: Subject to any disclaimer, the term of this patent is extended or adjusted under 35 U.S.C. 154(b) by 127 days.

(21) Appl. No.: 13/002,312

(22) PCT Filed: Jul. 9, 2009

(86) PCT No.: PCT/GB2009/001713
§ 371 (c)(1), (2), (4) Date: Jan. 24, 2011

(87) PCT Pub. No.: WO2010/004289
PCT Pub. Date: Jan. 14, 2010

(65) Prior Publication Data
US 2011/0153083 A1 Jun. 23, 2011

(30) Foreign Application Priority Data

Jul. 9, 2008 (GB) .................................. 0812525.4

(51) Int. Cl.
*G05B 21/02* (2006.01)
(52) U.S. Cl.
USPC ..................... 700/266; 422/82.01; 422/82.02; 422/82.03; 422/82.04; 422/82.12; 422/82.13; 422/127; 422/128; 702/22; 702/30; 702/31; 702/32
(58) Field of Classification Search
CPC . G01N 35/08; G01N 35/085; G01N 21/3577; G01N 25/56; G01N 29/024; G01N 29/4481; C02F 5/02; C02F 5/08
USPC ............. 422/82.01–82.04, 82.12, 82.13, 127, 422/128; 700/266; 702/22, 30–32
See application file for complete search history.

(56) References Cited

U.S. PATENT DOCUMENTS 5,493,631 A * 2/1996 Huang et al. ..................... 706/23
5,822,740 A * 10/1998 Haissig et al. ..................... 706/3
6,532,454 B1 * 3/2003 Werbos ........................... 706/14

FOREIGN PATENT DOCUMENTS

| EP | 0990898 A1 | 4/2000 |
| WO | WO0204916 A2 | 1/2002 |
| WO | WO2006054076 A1 | 5/2006 |

OTHER PUBLICATIONS

Clay et al: *Acoustical Oceanography: Principles and Applications*; John Wiley & Sons Inc., New York; 1997; pp. 2-11(Book).
Jerie et al: "Electrolytic solutions in ethylene glycol: ultrasonic and positron annihilation studies"; Physics Letters A; vol. 323; 2004; pp. 148-153.
Vibhu et al: "Ultrasonic and IR investigation of N—H—N complexes in ternary mixtures"; Journal of Molecular Liquids; vol. 115; 2004; pp. 1-3.
Goodenough et al: "Detection and quantification of insoluble particles by ultrasound spectroscopy"; Ultrasonics; vol. 43; 2005; pp. 231-235.

*Primary Examiner* — Shogo Sasaki
(74) *Attorney, Agent, or Firm* — W. Kevin Ransom; Moore & Van Allen PLLC

(57) ABSTRACT

A method for analyzing a fluid containing one or more analytes of interest includes; measuring a plurality of properties of a sample fluid with unknown concentrations of the one or more analytes of interest; and using the measurements and a model of the relationship between the plurality of properties and concentrations of the one or more analytes to calculate the concentration of at least one of the analytes of interest. The model may be an artificial neural network. The method may be used to monitor the concentration of inhibitors of gas hydrate formation in a fluid. Apparatus for use in the method is also provided.

15 Claims, 5 Drawing Sheets

(56) References Cited

OTHER PUBLICATIONS

Vyas et al: "A non-invasive ultrasonic gas sensor for binary gas mixtures"; Sensors and Actuators B; vol. 115; 2006; pp. 28-32.

Misra et al: "Ultrasonic velocity, viscosity, density and excess properties of binary mixture of dimethyl sulphoxide with propanoic acid and n-butyric acid"; Journal of Molecular Liquids, Elsevier, Amsterdam, NL; vol. 135, No. 1-3; May 5, 2007; pp. 166-169.

International Search Report for PCT/GB2009/001713 dated Dec. 28, 2009.

* cited by examiner

HYDRATE MONITORING SYSTEM

FIELD OF THE INVENTION

The present invention relates to methods and apparatus for measurement of the concentration of analytes of interest in a fluid. The methods and apparatus have particular applicability to the fields of petroleum and production engineering, gas processing, glycol regeneration, flow assurance, for example in preventing gas hydrate formation in process pipelines.

BACKGROUND TO THE INVENTION

The past decade has witnessed dramatic changes in the oil and gas industry with the advent of deep-water exploration and production. A major challenge in deep water field development is to ensure unimpeded flow of hydrocarbons to the host platform or processing facilities. Managing solids such as hydrate, waxes, asphaltene and scale is the key to the viability of developing a deep-water prospect.

The oil industry is facing a flow assurance issue with hydrate deposits in pipelines where hydrate often forms at inaccessible locations. One of the problems other than blockage is the movement of the hydrate plugs in the pipeline at high velocity, which can cause rupture in the pipeline. Any blockage in an oil/gas pipeline due to hydrate is a serious threat to the economic and cost effective strategy and also personnel safety.

The conventional way to prevent and reduce hydrate risks in transfer line and process facilities is to remove one of the elements favouring hydrate formation. For example, thermal insulation and external heating techniques are used to remove the low temperature element. Water can be removed by dehydration of the natural gas using glycol system and lowering the operating pressure can reduce the tendency for hydrate to form in the production system. However, these conventional techniques may not be feasible for some fields especially in offshore and deepwater environments due to space limitation and high insulation, heating and capital costs. Deepwater insulated pipeline costs are reported typically US$1 million per km of flowline.

Another option is to use the so-called "Thermodynamic Inhibitors". These are water-soluble chemicals that reduce the water activity, hence shifting the hydrate phase boundary to higher pressure and/or lower temperature conditions. The common industry practice is to use methanol (MeOH) and/or mono ethylene glycol (MEG). However, due to high dosage requirement it can result in significant increase in CAPEX and OPEX, in particular at high water cut conditions, as well as logistical and environmental problems.

In recent years, the industry has focused on the application of Low Dosage Hydrate Inhibitors (LDHIs). LDHIs are classified into Kinetic Inhibitors (KIs) and Anti-Agglomerates (AAs). The KIs work by delaying nucleation and growth of crystals. However, they generally fail to inhibit the agglomeration of crystals once nucleation occurs. AAs allow gas hydrates to form but prevent the agglomeration of hydrate crystals and thus minimize the risk of pipeline plugging.

Current industry practice for hydrate prevention is injecting hydrate inhibitors at the upstream end of pipelines based on the calculated/measured hydrate phase boundary, water cut, worst pressure and temperature conditions, and the amount of inhibitor lost to non-aqueous phases. In general, systematic ways of controlling and monitoring along the pipeline and/or downstream to examine the degree of inhibition are very limited.

SUMMARY OF THE INVENTION

According to a first aspect, the present invention provides a method for analysing a fluid containing one or more analytes of interest to determine the concentration of one or more of the analytes comprising:
   measuring a plurality of properties of a sample fluid with unknown concentrations of the one or more analytes of interest; and
   using the measurements and a model of the relationship between the plurality of properties and concentrations of the one or more analytes to calculate the concentration of at least one of the analytes of interest.

Using this technique, there is provided a simple and effective way to determine the concentration of one or more analytes, even when the measured physical property is dependent on multiple components in the fluid.

Suitable properties of a fluid that may be measured include, but are not limited to electrical conductivity, sound velocity, temperature, rate of change of sound velocity with temperature and rate of change of electrical conductivity with temperature. Sound velocity and electrical conductivity are preferred properties.

The model may be developed using measurements of one or more of properties from samples having known concentrations of the one or more analytes. Preferably, the model is an artificial neural network that is trained using the measured properties and the known concentration(s) of the one or more analytes of interest in the test fluid. This is a useful approach for correlating a limited quantity of experimental data with required variables in some specific cases where there is a lack of fundamental understanding of the relationship between the variables under examination. The mathematics and methods of utilising artificial neural networks are well known to a skilled man. The process of deriving and optimising a suitable neural network for carrying out the methods of the present invention is described more fully hereafter with reference to specific examples.

The fluid tested by the method may be, for example water from a hydrocarbon pipeline. Such pipelines are susceptible to solidification due to the formation of gas hydrates under appropriate temperature and pressure conditions such as can be found in the oil and gas industry production, process transport pipelines. As discussed above, the formation of gas hydrates is prevented by the addition of Low Dosage Hydrate Inhibitors (LDHIs). In addition to salts, which may already be present in produced water in a hydrocarbon stream, further quantities of inhibitors, for example thermodynamic inhibitors, may be added, such as alcohol(s). These hydrate inhibitors, typically salts and organic compounds, in the system inhibit hydrate formation. It is essential that an appropriate hydrate safety margin be maintained. The hydrate safety margin being a sufficient excess of the inhibitors to ensure that, even allowing for foreseeable changes to the conditions (for example to temperature, concentrations and/or pressure) no dangerous hydrate formation should be expected.

The salt and/or the inhibitor (i.e., organic inhibitor and/or low dosage hydrate inhibitor) concentrations are therefore monitored to ensure that an appropriate concentration of inhibitor is maintained i.e. the salt and/or organic inhibitors are two analytes of interest that can be measured by the method of the invention. To this end the method may further involve using the concentration to determine a safety margin for one or more of the analytes. For example, where the one or more analyte is a hydrate formation inhibitor, the method may be used to determine the hydrate safety margin. In other systems containing other types of analytes of interest, which are required to be at a suitable concentration, a safety margin for one or more of these analytes may be determined.

Typically the method is used to determine the concentration of two analytes of interest. For example, the method may be used to determine the concentrations of both ionic and non-ionic analytes of interest, for example salt(s) and alcohol(s) in aqueous fluids.

The method may be employed to determine the concentration of analytes of interest in many applications. The method can measure low concentrations of an analytes. For example where the electrical conductivity and sound velocity are the measured properties it can be possible to determine an analyte concentration of 0.1 mass % or even lower.

Examples of other uses in oil industry applications include the determination or monitoring of the concentration of MEG (monoethylene glycol), DEG (diethylene glycol) or TEG (triethylene glycol) in fluids that are processed in the regeneration units that recover these substances for reuse as additives.

The method of the invention is not restricted to use in aqueous systems but can be used with other fluids, for example organic liquids. Indeed the method can be used to determine the water content in an organic liquid. For example, the water content in DME (dimethoxyethane).

The testing of a sample fluid to determine the concentration of the analyte or analytes of interest may be carried out on a sample withdrawn from the bulk. For example, the sample may be removed from a pipeline or tank and tested in the laboratory. Preferably an on-line sampling method is used. Appropriate sensors located in a pipeline, for example, may be used to measure the online physical properties.

Measurement of electrical conductivity and sound velocity are particularly preferred as these two properties are largely independent of each other and both properties can be measured on-line, using sensors, which do not interfere with the operation of a pipeline for example. Produced water in oilfield operations generally contains salts; however, the concentration of salts may not be adequate for preventing gas hydrate formation. As a result more salts and/or organic inhibitors such as alcohols are added to the system. Salts increase the conductivity of aqueous solutions, whereas, alcohols reduce the conductivity.

While conductivity measurements alone could be used to determine the concentration of salt or alcohol, it would not be very accurate for systems containing both salts and alcohols, as similar conductivity values could result from various combinations of salts and alcohols. The method of the invention can be used to overcome this problem by combining conductivity measurements with a second physical parameter, for example with sound velocity measurements. The velocity of sound in a fluid relates to the density and bulk modulus, and therefore the concentration of salts and/or organic components in produced water.

Electrical conductivity of liquid solutions depends on the concentration of ions and their activity and is directly proportional to the salt concentration. The activity of the ions will be affected by temperature, and impurities such as nonconductive chemical additives. Therefore, it is possible to use electrical conductivity as an indicating parameter to measure the concentration of hydrate inhibitors that normally are non-electrolytes. To be able to determine both organic inhibitor and salt concentrations simultaneously, an additional physical parameter measurement is required. Suitable parameters should be independent of conductivity, i.e., it should not be correlated with electrical conductivity. Furthermore the second parameter should be capable of measurement sensitive enough to identify the changes in both organic hydrate inhibitor concentrations and salt concentrations as well. Ideally the parameter should be capable of measurement on-line (In other words, the technique is expected to be applicable under practical pipeline conditions).

Sound velocity has been found to be a suitable parameter. It is well known that the velocity of sound propagation can be directly related to salt concentration.[Ref 1] Recent literature shows that sound velocity has been successfully applied to investigate a variety of solutions, even composition of binary gas mixtures.[Refs 2-5] Typically ultrasound frequencies are employed, for example a frequency of 1 MHz. The ultrasound velocity measurement can be an ideal technique for online applications as well. Ultrasound can penetrate metal walls of pipelines, and is not easily interfered by unexpected waves like common sound and low frequency vibration. The preferred method therefore combines sound velocity measurement with electrical conductivity measurement, to provide an integrated Conductivity-Sound Velocity method. Preferably ultrasound frequencies are used.

Thermal parameters of properties of a fluid being tested can also be determined and used in the method of the invention. For example the coefficient of sound velocity with temperature ($\Delta V/\Delta T$) or the coefficient of electrical conductivity with temperature ($\Delta \sigma/\Delta T$) can each be a property of a sample fluid used in the calculation of the concentration of analytes of interest. For example in an aqueous system liable to hydrate formation there may be three inhibitors (salts, an organic inhibitor and a low dosage hydrate inhibitor). Determination of the concentration of all three inhibitors (analytes of interest) can be achieved by determining sound velocity, electrical conductivity and one of the coefficient of sound velocity with temperature or the coefficient of electrical conductivity with temperature.

Physical properties such as conductivity, temperature and sound velocity can be readily measured in a fluid in either an off-line (testing removed samples) or on-line manner. Preferably the properties are measured continuously and on-line. Alternatively on-line monitoring can be carried out using a sample cell in communication with a pipeline or vessel. The sample cell is filled periodically (or continuously in the case of a pipeline) with a sample of fluid and analysed by the method of the invention.

For monitoring particularly critical analyte concentrations, for example the concentration of hydrate inhibitors in a pipeline, continuously monitoring the system provides the earliest possible warning of changes allowing remedial action to be taken as soon as possible. The remedial action can be for example the introduction of more hydrate inhibitors to the system or the shut down of flow.

According to a second aspect the present invention provides a method for controlling the concentration of at least one analyte of interest in a fluid comprising using the method of the first aspect of the invention to calculate the concentration of the at least one analyte and further comprising adjusting the concentration of the analyte of interest in the fluid depending on the calculated concentration.

The concentrations of all of the analytes of interest may be determined. Adjustments can then be made to any or all of the concentrations as required. The adjustment of the concentration of analytes of interest can be carried out in different ways depending on the situation. The concentration of analytes can be reduced, if required, by reducing the analyte's injection rate or by adding fluid that does not contain the analyte(s). Alternatively if a higher concentration of analytes is required then more analyte can be added. For example, adding more hydrate inhibitor to maintain the hydrate safety margin in a pipeline.

The adjustments of concentration may be carried out automatically, in response to on-line measurement results. Once the model, for example a neural network, has been trained to provide sufficiently accurate concentration measurements the method of adjusting analyte concentration can be operated automatically. The on-line measurements are used to control appropriate additions, for example introduction of hydrate inhibitor through an automated/manual valve or pump into a pipeline.

Suitable apparatus for carrying out the methods of the invention where electrical conductivity and sound velocity measurements are made constitutes another aspect of the present invention.

According to a third aspect the present invention provides an apparatus for determining the concentration of one or more analytes of interest in a fluid comprising:
- a conductivity sensor for measuring the fluid electrical conductivity;
- means for measuring the velocity of sound in the fluid; and
- means for determining the concentration of at least one of the analytes of interest using the electrical conductivity and sound velocity measurements.

The means for measuring the velocity of sound may comprise at least one transducer for inter-conversion of sound and electrical signals, a transmitter producing electrical signals for conversion to sound signals by a transducer, a receiver for receiving electrical signals converted from sound signals by a transducer and an analyser for calculating velocity of sound in a fluid sample from transmitted and received signals. Preferably the sound signals produced and received by the transducer or transducers are ultrasound. Typically a frequency of 1 MHz is employed.

The apparatus may have only one transducer, which both generates sound signals to the sample being analysed and receives sound signals back from the sample, for example by reflection from a portion of the wall of a vessel containing the sample. The apparatus may additionally comprise a reflector for directing sound signals back to the transducer.

Alternatively the apparatus may have two transducers. Where two transducers are used they may, for example, be disposed at opposite sides of a vessel or pipe containing the sample. In this case one transducer can act as a transmitter of sound signals through a fluid sample and the other as receiver.

The transmitter and the receiver of electrical signals may be combined as a single transmitter/receiver device. Conveniently the transmitter/receiver may also include the analyser, which calculates the velocity of sound in the sample.

The means for determining the concentration the electrical conductivity and sound velocity measurements may be a computer provided with suitable software for carrying out artificial neural network training and analysis.

Advantageously the electrical conductivity sensor may also comprise temperature-measuring capability. Alternatively the apparatus may further comprise an alternative temperature measuring means i.e. a separate thermometer.

Temperature measurement is required where the temperature of the fluids being tested may vary as sound velocity and electrical conductivity varies with temperature. Advantageously the temperature measurement can be employed as a third property of the fluid to allow determination of a further analyte of interest. Advantageously the coefficient of sound velocity and/or conductivity with temperature may be used as a measured property of the fluid as discussed hereafter with reference to a specific example.

The apparatus may include a sample cell. The sample cell is constructed to be suitable for the fluids being tested and the conditions of test required. For example for hydrate inhibition testing the sample cell may be a pressure-containing vessel, so that samples can be tested under pipeline conditions. The sample cell may also be temperature controlled so that temperature of different fluids tested may be kept constant or varied in a controlled manner as required.

The sample cell may be constructed for laboratory (bench) use. Alternatively and advantageously in pipeline applications the sample cell may be an online sample cell, fitted to a pipeline. For example the sample cell may be or may not be located in a loop section of pipework connected to a pipe by appropriate valves (a bypass). The valves are operated to introduce a sample of the fluid flowing in the pipe to the loop section where testing can be carried out. The testing can be continuous by allowing the fluid to flow continuously around the loop if desired.

Alternatively the sample cell may simply be a section of the pipe through which a fluid flows, fitted at least with the electrical conductivity sensor and at least one sonic transducer preferably an ultrasonic transducer.

Where used in online applications the sample cell may be fitted with heating elements, for example Peltier type heating elements, to enable the local temperature of the fluid to be changed. This will allow temperature related measurements, for example the thermal coefficient of sound velocity or of electrical conductivity, to be used.

According to yet another aspect of the invention, there is provided a method for determining the concentration of one or more analytes in a fluid comprising measuring two or more of the electrical conductivity of the fluid; the velocity of sound in the fluid and the temperature of the fluid and using the two or more measurements to determine the concentration of at least one of the analytes.

The concentration may be determined using a neural network representative of the relationship between the various properties and the concentrations and trained using data from known samples.

Features of one aspect of the present invention may be applied to any other aspect in any suitable combination. For example features of the method may be applied to the apparatus and vice versa.

BRIEF DESCRIPTION OF THE DRAWINGS

Various aspects of the invention will now be described by way of example only and with reference to the following drawings, of which.

DETAILED DESCRIPTION OF EMBODIMENTS OF THE INVENTION

Example 1

Conductivity-Sound Velocity Method

Various combinations of glycol-salt aqueous systems have been investigated and the generated data (see Table 1 hereafter) were used in training an Artificial Neural Network (ANN).

Electrical conductivity and sound velocity were measured as a function of temperatures for a wide range of solutions: brine with 0, 1, 3, 5, 7, and 10 wt % of NaCl in water, ethylene glycol-brine (Combination of each brine with the previous NaCl concentrations with 0, 10, 20, 30, 40, and 50 wt % of ethylene glycol in total solution). Typical results for an ethylene glycol-brine system are shown in FIGS. 1 and 2.

Figure 1:
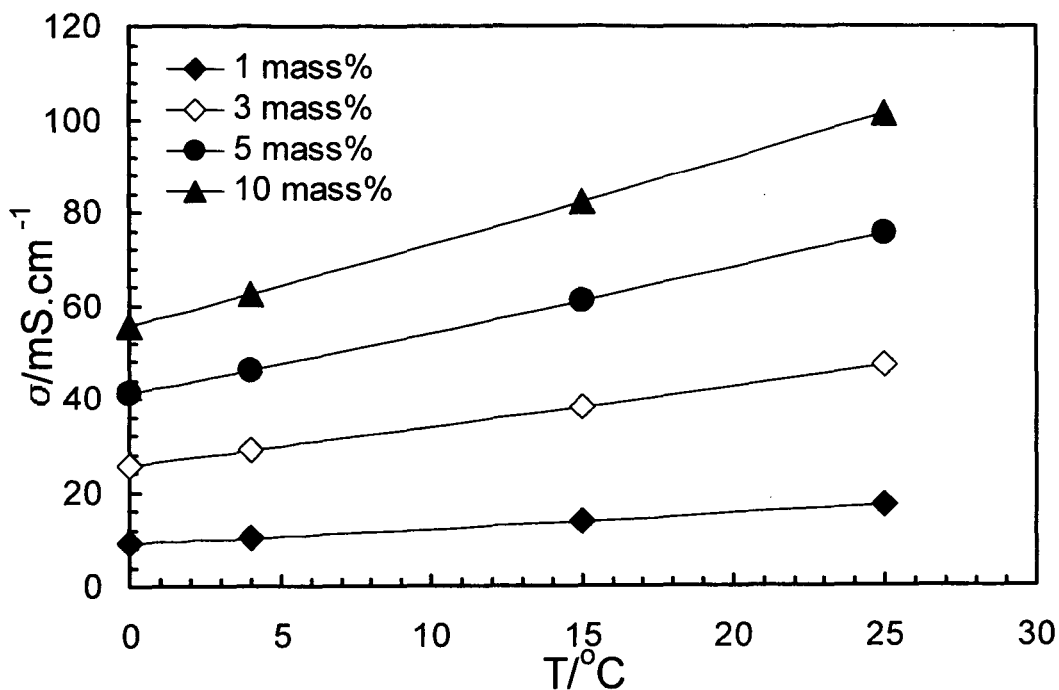
FIGS. 1, 2, 3, and 4 show the variation of measured electrical conductivity and sound velocity for aqueous solutions containing various concentrations of ethylene glycol and sodium chloride.
Figure 2:
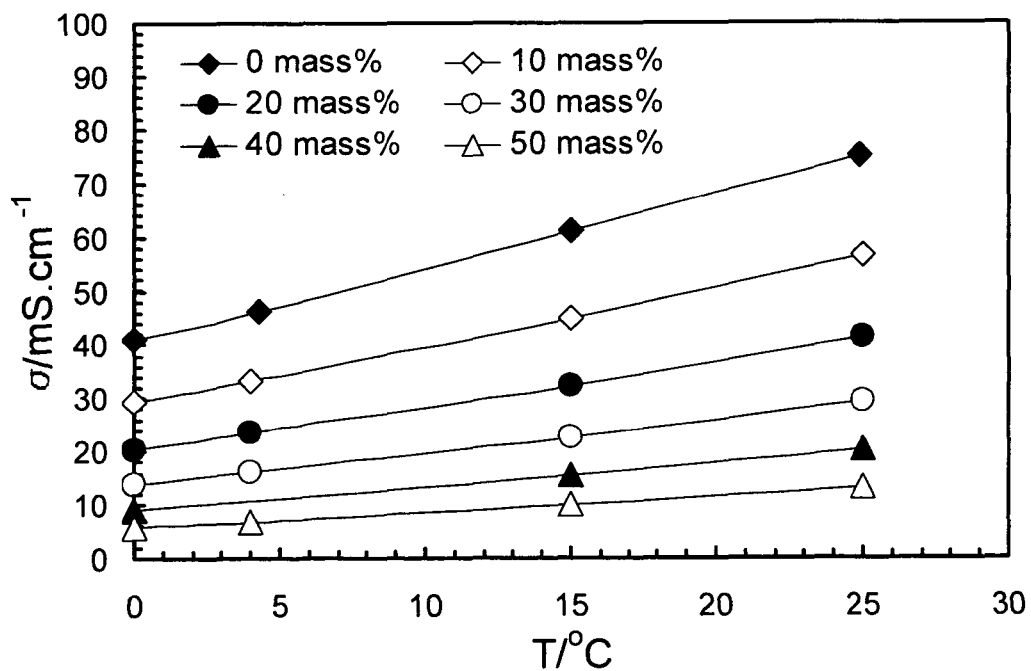

FIG. 1 shows the measured electrical conductivity of aqueous solutions containing various concentrations of brine (NaCl at 1, 3, 5 and 10% by mass) plotted against temperature. FIG. 2 shows the electrical conductivity of various concentrations of ethylene glycol with (a typical) 5 wt % of NaCl, plotted against temperature. These figures show that as both brine concentration and ethylene glycol concentration affect the electrical conductivity, electrical conductivity alone cannot be used to determine the NaCl and/or ethylene glycol content of a solution containing variable amounts of both.

Figure 3:
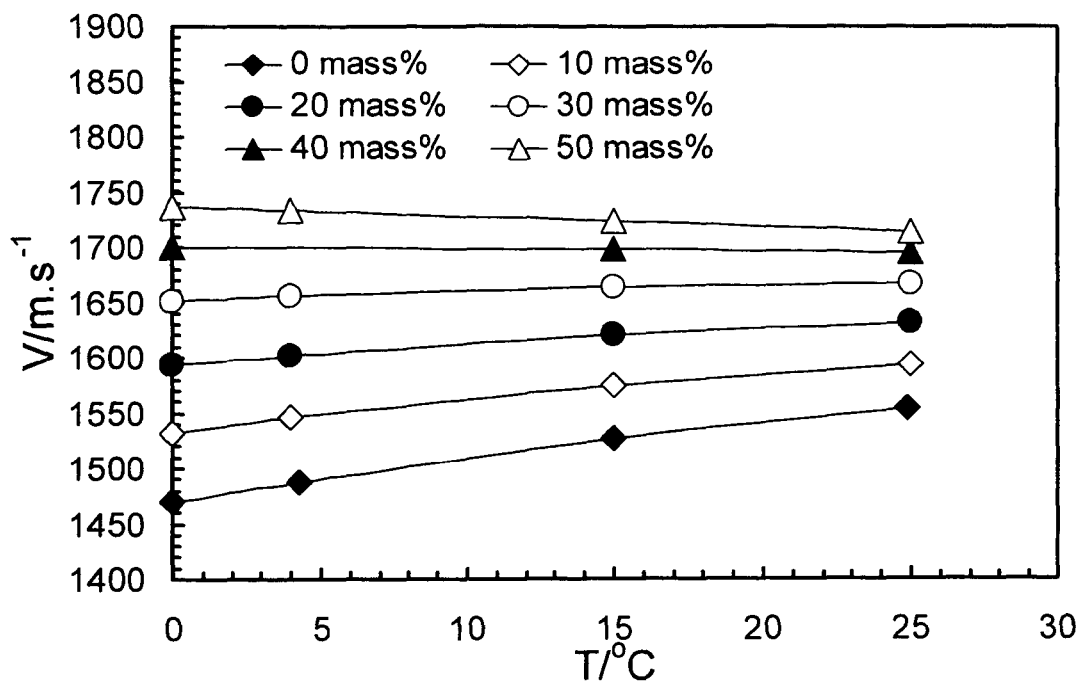
Figure 4:
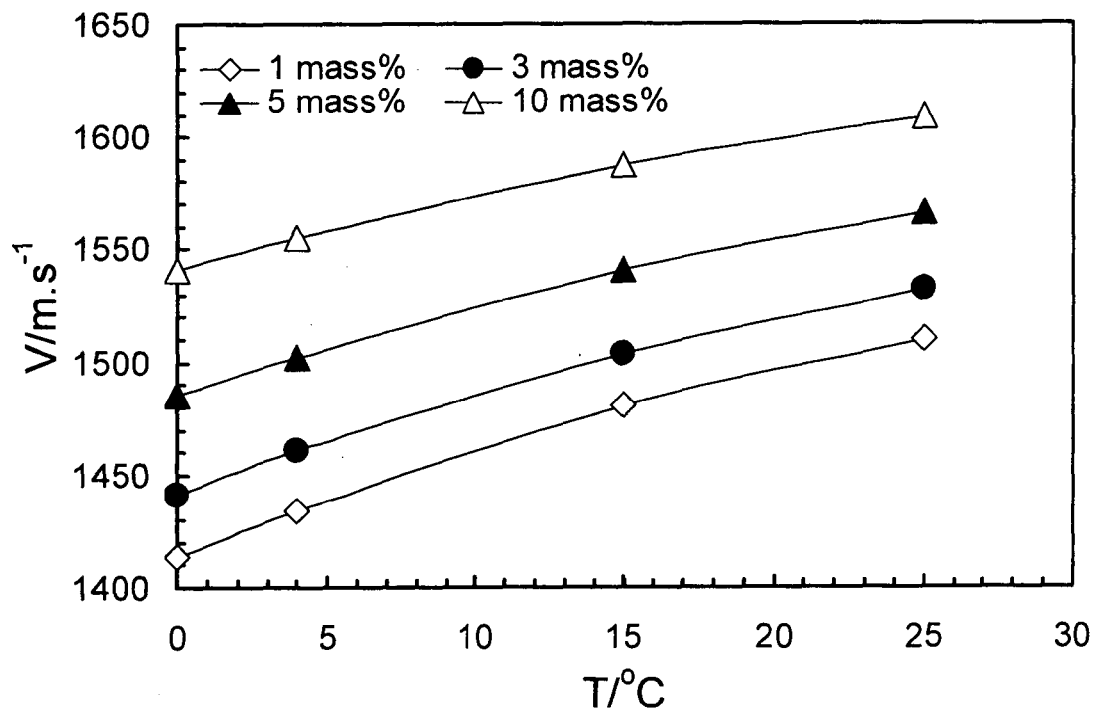

FIG. 3 shows the sound velocity changes with varying concentrations of ethylene glycol, from 0 to 50 mass % in the presence of 5 wt % of NaCl in water. Similar variation in sound velocity is obtained when the NaCl content of a solution is varied as shown in FIG. 4. Therefore neither sound velocity nor electrical conductivity measurements alone can be used for determination of NaCl and ethylene glycol contents in solutions containing variable amounts of both.

Figure 5:
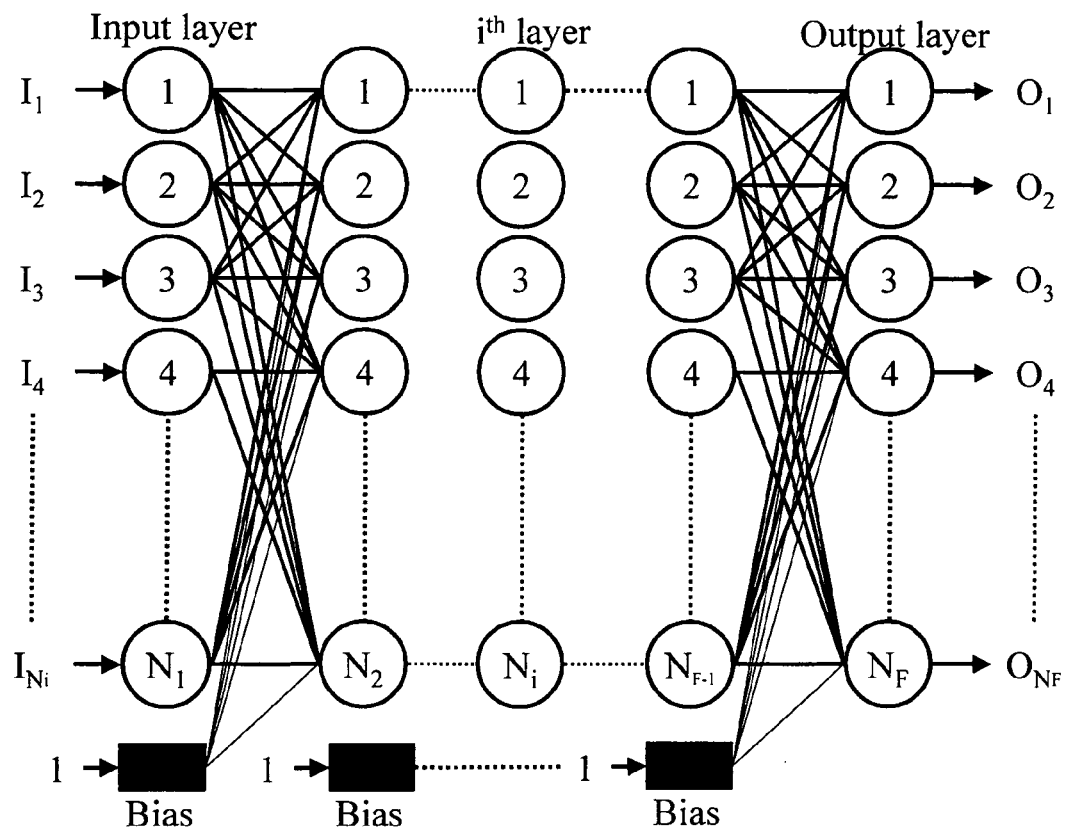
FIG. 5 illustrates schematically the structure of an artificial neural network (ANN)

Artificial neural network (ANN) correlations were then developed to determine inhibitor (ethylene glycol) concentration and salt concentration simultaneously using the measured electrical conductivity, sound velocity, and temperature. The methods described here use the creation and use of an artificial neural network, although other techniques can be used to model the fluid as a function of the concentration of the analytes of interest and the measured properties. An artificial neural network consists of large numbers of computational units called neurons, connected to each other by means of direct weighted communication links as shown in FIG. 5.

The input layer of the network receives all the input data and introduces scaled data to the network. The data from the input neurons are propagated through the network via weighted interconnections. Every i neuron in a k layer is connected to every neuron in adjacent layers. The i neuron within the hidden k layer performs the following tasks: summation of the arriving weighted inputs (input vector $I_i = [I_{i,1}, \ldots I_{i,NK-1}]$) and propagations of the resulting summation through a non-linear activation function, f, to the adjacent neurons of the next hidden layer or to the output neuron(s). A bias term, b, is associated with each interconnection in order to introduce a supplementary degree of freedom. The expression of the weighted sum, S, to the $i^{th}$ neuron in the $k^{th}$ layer ($k \geq 2$) is:

$$S_{k,i} = \sum_{j=1}^{N_{k-1}} [(w_{k-1,j,i} I_{k-1,j}) + b_{k,i}] \quad (1)$$

where w is the weight parameter between each neuron-neuron interconnection. Using this simple feed-forward network with non-linear activation functions, the output, O, of the i neuron within the hidden k layer is therefore:

$$O_{k,i} = f\left(\sum_{j=1}^{N_{k-1}} [(w_{k-1,j,i} I_{k-1,j}) + b_{k,i}]\right) = f(S_{k,i}) \quad (2)$$

During the training, input variables are fed to the network and the difference between the experimental outputs and the calculated outputs is used as a criterion for adjustment of network's synaptic weights. All synaptic weights and biases are first initialised randomly. The network is then trained; its synaptic weights are adjusted by an optimisation algorithm, until it correctly emulates the input/output mapping, by minimizing the average root mean square error.

For the ethylene glycol-brine (NaCl) system, more than 124 sound velocity and conductivity data at known temperatures were measured. This assembled data set was subdivided into 3 classes: training (approximately, 50%), validation (approximately, 25%) and test set (approximately 25%), having the same repartition of data (same range of temperature, conductivity, sound velocity and concentrations). After partitioning of the data set, the training-set was used to tune the parameters, i.e. determination of the optimum values of synaptic weights and biases. The validation-set was used during the adjustment of the network's synaptic weights to evaluate the algorithms performance on independent data and stop the tuning if the error on the validation set increases. The validation-set is not an independent data set but does not have any influence in the parameter fitting procedure. Finally, the test-set measures the generalization ability of the model after the fitting process.

To find the optimal network architecture, a trial/error procedure was applied, in which the structure of the network is changed and the resulting network was trained, validated and tested using the previously described algorithm and procedures. If the number of neurons were too small, the network would fail to train correctly and the overall accuracy of the network would suffer from it. However, a network with too many nodes can fail to capture the underlying relationship between input and output variables. The overall tuning and validation test accuracy of the network and the test-set accuracy are used to compare the performance of the various network trial architectures.

For example for this system, without a validation procedure, a two-hidden layer neural network that has 7 nodes in the hidden layer can be trained with excellent accuracy described in absolute average deviation (AAD) (AAD=AAD$_{EG}$+AAD$_{NaCl}$=3.5%). [AAD$_{EG}$ is the AAD of the ethylene glycol results and AAD$_{NaCl}$ is the AAD of the sodium chloride results]. However the network predicts independent data much less accurately (AAD=12.5%). Adding the validation procedure, increases the prediction accuracy of the network (AAD=5.1%) but impairs the training accuracy (AAD=4.1%).

After training the best structure was observed with a two-hidden layer network with 7 nodes on each layer. The range of temperatures and compositional data used in input is given in Table 1 below.

TABLE 1

Range Of Input/Output Data

| Inputs/Output | Min | Max |
| --- | --- | --- |
| T (° C.) | 0 | 25 |
| σ (mS · cm$^{-1}$) | 1.3 | 102.5 |
| V (m · s$^{-1}$) | 1400 | 1760 |

TABLE 1-continued

Range Of Input/Output Data

| Inputs/Output | Min | Max |
|---|---|---|
| $X_{EG}$ (wt %) | 0 | 50 |
| $X_{NaCl}$ (wt %) | 1 | 10 |

T=temperature: σ=electrical conductivity: V=sound velocity: $X_{EG}$=concentration of ethylene glycol: $X_{NaCl}$=concentration of sodium chloride.

The test-set results are given in Table 2 below. Exp. denotes the experimental i.e. actual measured concentration ($X_{NaCl}$ or $X_{EG}$) of the analyte. ANN denotes the concentration ($X_{NaCl}$ or $X_{EG}$) of the analyte as determined by the Artificial Neural Network.

TABLE 2

Training and validation data for the ethylene glycol system

| Input | | | Output | | | |
|---|---|---|---|---|---|---|
| | | | $X_{NaCl}$ (wt %) | | $X_{EG}$ (wt %) | |
| T/° C. | σ/mS · cm$^{-1}$ | V/m · s$^{-1}$ | Exp. | ANN | Exp. | ANN |
| Training data | | | | | | |
| 0 | 6.656 | 1483.2 | 1.0 | 1.0 | 10 | 10 |
| 4 | 7.585 | 1497.92 | 1.0 | 1.0 | 10 | 10 |
| 15 | 10.32 | 1531.66 | 1.0 | 1.0 | 10 | 10 |
| 25 | 13.04 | 1553.74 | 1.0 | 1.0 | 10 | 10 |
| 0 | 4.677 | 1551.9 | 1.0 | 1.0 | 20 | 20 |
| 4 | 5.374 | 1561.27 | 1.0 | 1.1 | 20 | 21 |
| 15 | 7.473 | 1582.79 | 1.0 | 1.0 | 20 | 20 |
| 25 | 9.612 | 1596.97 | 1.0 | 1.0 | 20 | 20 |
| 0 | 3.177 | 1616.7 | 1.0 | 1.0 | 30 | 30 |
| 15 | 5.238 | 1631.89 | 1.0 | 1.0 | 30 | 30 |
| 25 | 6.837 | 1636.52 | 1.0 | 1.0 | 30 | 30 |
| 0 | 2.113 | 1672.3 | 1.0 | 1.0 | 40 | 40 |
| 4 | 2.469 | 1673.24 | 1.0 | 1.0 | 40 | 40 |
| 15 | 3.583 | 1673.46 | 1.0 | 1.0 | 40 | 40 |
| 25 | 4.763 | 1670.65 | 1.0 | 1.0 | 40 | 40 |
| 0 | 1.335 | 1715.9 | 1.0 | 1.0 | 50 | 50 |
| 4 | 1.571 | 1714.11 | 1.0 | 1.0 | 50 | 49 |
| 15 | 2.318 | 1706.51 | 1.0 | 1.0 | 50 | 49 |
| 25 | 3.123 | 1696.2 | 1.0 | 1.0 | 50 | 51 |
| 0 | 18.51 | 1508 | 3.0 | 2.9 | 10 | 10 |
| 4 | 21 | 1521.48 | 3.0 | 3.0 | 10 | 10 |
| 15 | 28.36 | 1552.94 | 3.0 | 3.0 | 10 | 10 |
| 0 | 12.87 | 1572.4 | 3.0 | 2.9 | 20 | 20 |
| 4 | 14.8 | 1581.47 | 3.0 | 3.0 | 20 | 20 |
| 15 | 20.53 | 1601.75 | 3.0 | 3.0 | 20 | 21 |
| 25 | 26.32 | 1614.25 | 3.0 | 2.9 | 20 | 20 |
| 0 | 8.759 | 1634 | 3.0 | 3.0 | 30 | 29 |
| 4 | 10.16 | 1638.64 | 3.0 | 3.0 | 30 | 30 |
| 15 | 14.41 | 1647.77 | 3.0 | 2.9 | 30 | 30 |
| 25 | 18.75 | 1651.48 | 3.0 | 3.0 | 30 | 30 |
| 0 | 5.783 | 1686.1 | 3.0 | 3.0 | 40 | 40 |
| 4 | 6.759 | 1687.09 | 3.0 | 3.1 | 40 | 41 |
| 15 | 9.787 | 1686.76 | 3.0 | 3.0 | 40 | 41 |
| 25 | 12.98 | 1682.55 | 3.0 | 3.1 | 40 | 40 |
| 0 | 3.626 | 1726.6 | 3.0 | 2.9 | 50 | 50 |
| 4 | 4.285 | 1724.25 | 3.0 | 3.0 | 50 | 50 |
| 15 | 6.362 | 1715.95 | 3.0 | 3.0 | 50 | 50 |
| 25 | 8.586 | 1706.08 | 3.0 | 3.0 | 50 | 50 |
| 0 | 29.47 | 1532.3 | 5.0 | 5.1 | 10 | 10 |
| 4 | 33.39 | 1545.41 | 5.0 | 5.0 | 10 | 10 |
| 15 | 45 | 1575.03 | 5.0 | 4.8 | 10 | 10 |
| 25 | 56.61 | 1593.74 | 5.0 | 5.1 | 10 | 10 |
| 0 | 20.47 | 1593.8 | 5.0 | 5.1 | 20 | 20 |
| 4 | 23.51 | 1601.97 | 5.0 | 5.1 | 20 | 19 |
| 15 | 32.49 | 1620.41 | 5.0 | 5.0 | 20 | 20 |
| 25 | 41.46 | 1632.06 | 5.0 | 5.0 | 20 | 20 |
| 0 | 13.85 | 1650.8 | 5.0 | 4.8 | 30 | 29 |
| 4 | 16.04 | 1655.19 | 5.0 | 5.2 | 30 | 30 |
| 15 | 22.71 | 1663.49 | 5.0 | 5.4 | 30 | 31 |
| 25 | 29.57 | 1666.23 | 5.0 | 5.9 | 30 | 32 |
| 0 | 9.083 | 1700.4 | 5.0 | 4.9 | 40 | 40 |
| 15 | 15.39 | 1699.13 | 5.0 | 4.9 | 40 | 40 |
| 25 | 20.37 | 1695.13 | 5.0 | 4.9 | 40 | 40 |
| 0 | 5.717 | 1736.9 | 5.0 | 5.2 | 50 | 51 |
| 4 | 6.737 | 1733.9 | 5.0 | 5.2 | 50 | 50 |
| 15 | 9.956 | 1724.59 | 5.0 | 5.1 | 50 | 50 |
| 25 | 13.41 | 1714.79 | 5.0 | 5.0 | 50 | 49 |
| 0 | 39.54 | 1557.3 | 7.0 | 7.2 | 10 | 10 |
| 4 | 44.88 | 1568.9 | 7.0 | 7.0 | 10 | 10 |
| 15 | 60.54 | 1595.8 | 7.0 | 6.8 | 10 | 10 |
| 25 | 76.03 | 1613.9 | 7.0 | 7.1 | 10 | 10 |
| 0 | 27.46 | 1615.5 | 7.0 | 7.0 | 20 | 20 |
| 4 | 31.44 | 1622.8 | 7.0 | 6.9 | 20 | 20 |
| 15 | 43.36 | 1639.2 | 7.0 | 7.0 | 20 | 20 |
| 25 | 55.41 | 1649.5 | 7.0 | 7.1 | 20 | 19 |
| 0 | 18.65 | 1668.5 | 7.0 | 7.1 | 30 | 29 |
| 4 | 21.59 | 1672.1 | 7.0 | 7.4 | 30 | 30 |
| 15 | 30.5 | 1678.9 | 7.0 | 7.6 | 30 | 32 |
| 25 | 39.63 | 1681.1 | 7.0 | 8.6 | 30 | 34 |
| 0 | 12.08 | 1714 | 7.0 | 7.0 | 40 | 39 |
| 4 | 14.12 | 1714.1 | 7.0 | 7.2 | 40 | 40 |
| 15 | 20.45 | 1712 | 7.0 | 7.2 | 40 | 40 |
| 25 | 27.1 | 1707.2 | 7.0 | 6.9 | 40 | 39 |
| 0 | 7.57 | 1747.3 | 7.0 | 6.9 | 50 | 51 |
| 4 | 8.941 | 1744.4 | 7.0 | 7.0 | 50 | 50 |
| 25 | 17.92 | 1723.4 | 7.0 | 6.7 | 50 | 49 |
| 0 | 53.27 | 1762.8 | 10.0 | 9.7 | 10 | 10 |
| 15 | 81.45 | 1748.67 | 10.0 | 9.7 | 10 | 10 |
| 25 | 102.17 | 1736.62 | 10.0 | 10.1 | 10 | 10 |
| 0 | 36.6 | 1736.5 | 10.0 | 10.5 | 20 | 19 |
| 4 | 41.95 | 1735.83 | 10.0 | 10.4 | 20 | 20 |
| 15 | 57.91 | 1731.94 | 10.0 | 10.2 | 20 | 20 |
| 25 | 74 | 1725.78 | 10.0 | 10.0 | 20 | 20 |
| 0 | 24.62 | 1697.9 | 10.0 | 9.7 | 30 | 30 |
| 4 | 28.51 | 1700.46 | 10.0 | 9.6 | 30 | 30 |
| 15 | 40.32 | 1704.59 | 10.0 | 9.2 | 30 | 30 |
| 25 | 52.52 | 1704.62 | 10.0 | 9.8 | 30 | 31 |
| 0 | 15.9 | 1649.3 | 10.0 | 9.8 | 40 | 42 |
| 15 | 27.12 | 1669.03 | 10.0 | 8.1 | 40 | 36 |
| 25 | 36.01 | 1676.58 | 10.0 | 7.4 | 40 | 32 |
| 4 | 11.82 | 1605.96 | 10.0 | 10.1 | 50 | 49 |
| 15 | 17.61 | 1629.12 | 10.0 | 10.4 | 50 | 50 |
| 25 | 23.83 | 1644.08 | 10.0 | 9.8 | 50 | 48 |
| 0 | 56 | 1605.3 | 3.0 | 2.8 | 25 | 24 |
| 4 | 62.8 | 1611.81 | 3.0 | 3.0 | 25 | 24 |
| 15 | 83 | 1626.2 | 3.0 | 3.0 | 25 | 26 |
| 25 | 102.5 | 1634.78 | 3.0 | 3.2 | 25 | 26 |
| 4 | 18.64 | 1655.55 | 10.0 | 9.5 | 40 | 41 |
| Validation data | | | | | | |
| 4 | 60.44 | 1759.49 | 10 | 9.7 | 10 | 10.1 |
| 25 | 35.73 | 1574.4 | 3 | 3.3 | 10 | 10.4 |
| 4 | 10.63 | 1700.62 | 5 | 5.0 | 40 | 40.2 |
| 4 | 3.687 | 1621.72 | 1 | 1.0 | 30 | 27.6 |
| 15 | 13.27 | 1734.6 | 7 | 7.0 | 50 | 49.9 |
| 0 | 9.99 | 1595.8 | 10 | 10.1 | 50 | 49.2 |

As it can be seen, the ANN was well trained, and generates good correlation results. The validation data shows the ability of the ANN to predict the concentrations of EG (ethylene glycol) and NaCl. The absolute average deviations for the training set were 1.6% for EG (ethylene glycol) and 2.5% for NaCl and for the independent data set 2.6% for EG and 2.5% for NaCl.

Example 2

Conductivity

Sound Velocity Method

The same methodology as in example 1 was employed but the aqueous mixtures tested contained various concentrations of sodium chloride NaCl and polyvinyl caprolactam (PV-Cap). PVCap is a component of some of the commercially available hydrate inhibitor solution Luvicap® EG (polyvinyl-caprolactam/ethylene glycol solution) available from BASF AG of Ludwigshafen Germany. Results are shown in Table 3 below where $X_{PVCap}$ denotes the concentration of PVCap in the system. As with the NaCl/EG system of example 1, the ANN can accurately predict the actual concentrations of NaCl and PVCap in mixtures.

TABLE 3

Training and validation data for the PVCap-NaCl systems

| Input | | | Output | | | |
|---|---|---|---|---|---|---|
| | | | $X_{NaCl}$ (wt %) | | $X_{PVCap}$ (wt %) | |
| T/° C. | σ/mS · cm$^{-1}$ | V/m · s$^{-1}$ | Exp. | ANN | Exp. | ANN |
| Training data | | | | | | |
| 0 | 9.198 | 1416.6 | 1.0 | 1.0 | 0.2 | 0.2 |
| 4 | 10.379 | 1436.12 | 1.0 | 1.0 | 0.2 | 0.2 |
| 25 | 17.313 | 1511.4 | 1.0 | 1.0 | 0.2 | 0.2 |
| 0 | 9.007 | 1421.8 | 1.0 | 1.0 | 1.0 | 1.0 |
| 4 | 10.169 | 1440.89 | 1.0 | 1.0 | 1.0 | 1.0 |
| 15 | 13.612 | 1485.25 | 1.0 | 1.0 | 1.0 | 1.0 |
| 25 | 17.057 | 1515.23 | 1.0 | 1.0 | 1.0 | 1.0 |
| 0 | 41.23 | 1471.0 | 5.0 | 5.0 | 0.2 | 0.2 |
| 4 | 46.38 | 1488.03 | 5.0 | 5.0 | 0.2 | 0.2 |
| 25 | 76.05 | 1554.65 | 5.0 | 5.0 | 0.2 | 0.2 |
| 4 | 45.35 | 1494.01 | 5.0 | 5.0 | 1.0 | 1.0 |
| 15 | 60.1 | 1533.29 | 5.0 | 5.0 | 1.0 | 1.0 |
| 25 | 74.6 | 1559.08 | 5.0 | 5.0 | 1.0 | 1.0 |
| 0 | 21.86 | 1438.9 | 2.49 | 2.5 | 0.5 | 0.5 |
| 15 | 32.78 | 1500.42 | 2.49 | 2.5 | 0.5 | 0.5 |
| 25 | 40.6 | 1529.4 | 2.49 | 2.5 | 0.5 | 0.5 |
| Validation data | | | | | | |
| 15 | 61.37 | 1527.7 | 5.0 | 5.0 | 0.2 | 0.2 |
| 15 | 13.857 | 1481.25 | 1.0 | 1.0 | 0.2 | 0.2 |
| 4 | 24.67 | 1457.42 | 2.49 | 2.5 | 0.5 | 0.4 |
| 0 | 40.29 | 1476.9 | 5.0 | 5.0 | 1.0 | 1.0 |

Example 3

Conductivity

Sound Velocity Method

To examine the feasibility of the method, a prototype device of the form shown in FIG. 7 discussed below was used to test produced water samples from oilfields. The produced water samples contained various salt components like NaCl, KCl, CaCl$_2$, MgCl$_2$, etc. For example, one of the produced water samples investigated was a mixture of formation water (salt content 4.97 wt %), ethylene glycol (25 wt %) and an unknown corrosion inhibitor. Electrical conductivity and velocity of sound in the produced water sample were measured and by inputting the measured parameters to the developed ANN correlations, hydrate inhibitor and salt concentrations were determined. The EG concentration was found to be 25.2 mass % and the equivalent NaCl concentration 5.07 wt %. This result shows that the presence of small amounts of other salt components, typical concentrations of corrosion inhibitors, and a limited amount of insoluble solid particles in the produced water do not significantly affect the applicability of the Conductivity-Sound Velocity technique. The method is therefore suitable for the determination of hydrate safety margins (degree of inhibition of hydrate formation) for real fluid samples.

Example 4

Conductivity, Sound Velocity and Thermal Coefficient of Sound Velocity Method The Conductivity-Sound Velocity Method can be developed further to measure a third analyte of interest by the addition of a third measurement, for example, the coefficient of the velocity of sound with temperature i.e. the rate of change of sound velocity with temperature. As an alternative the coefficient of electrical conductivity with temperature may be used. If desired all four properties—conductivity, sound velocity, coefficient of sound velocity with temperature and coefficient of electrical conductivity with temperature—may be employed.

Experiments were carried out as before but with an aqueous systems containing NaCl, EG (ethylene glycol) and PVCap (added as the commercially available Luvicap® EG solution containing 40% PVCap).

In addition to the measured electrical conductivity and sound velocity, thermal coefficient of sound velocity was also measured for the aqueous solutions with various concentrations of Luvicap, EG, and NaCl.

Figure 6A:
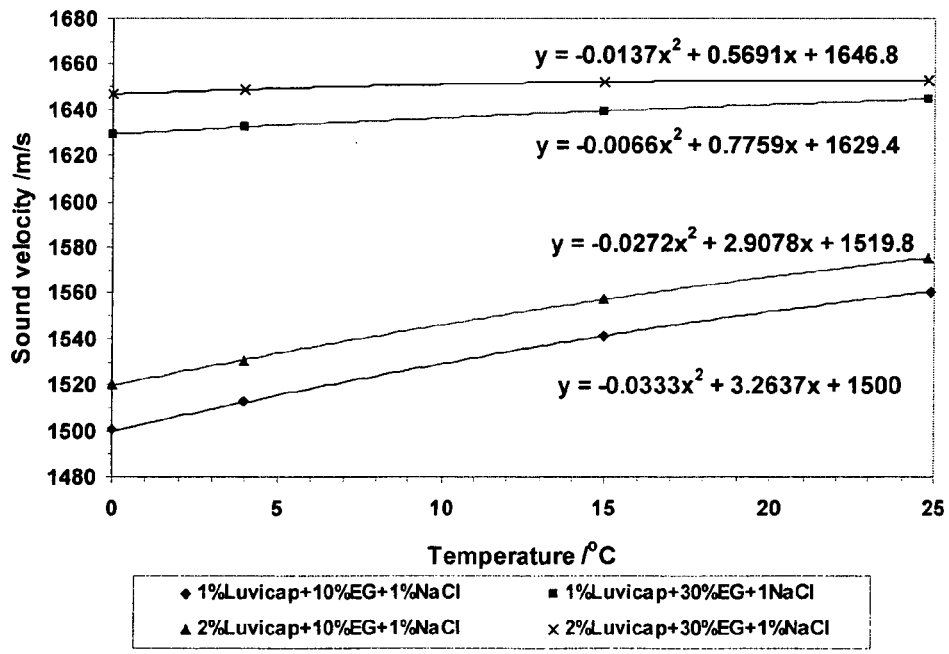
FIGS. 6a and 6b illustrate graphically the variation in sound velocity (6a) and of electrical conductivity (6b) of aqueous solutions containing sodium chloride, ethylene glycol and polyvinyl caprolactam.
Figure 6B:
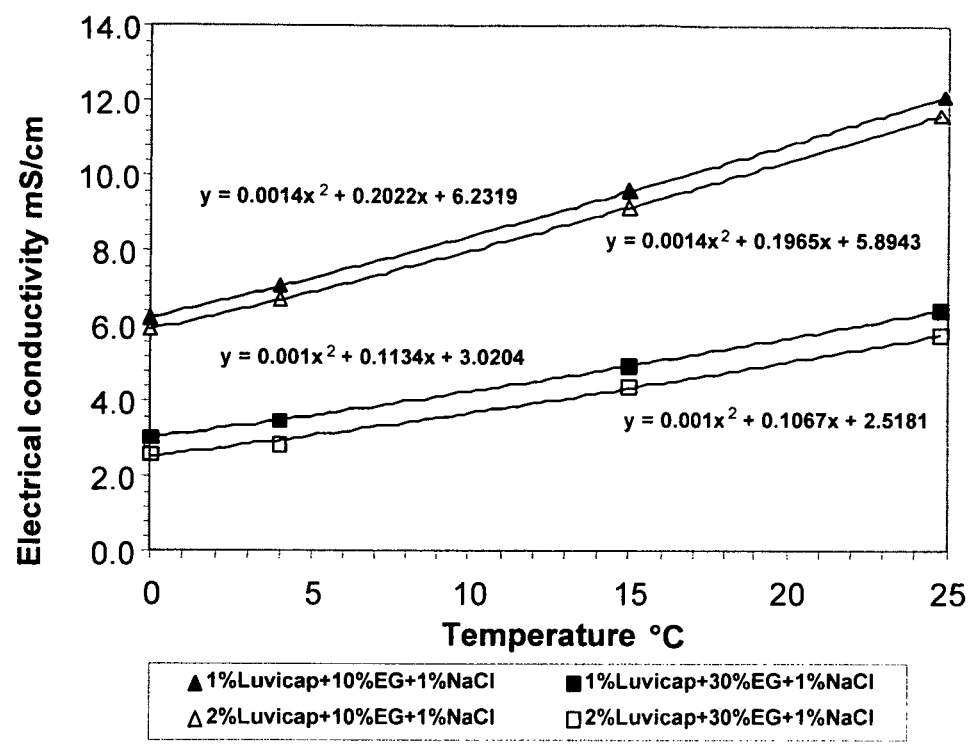

FIG. 6a shows graphically that addition of Luvicap® EG to aqueous EG solutions containing salts resulted in a measurable change in the sound velocity and in the thermal coefficient of sound velocity. Similar changes in the electrical conductivity and in the thermal coefficient of electrical conductivity can be seen in FIG. 6b, showing that thermal coefficient of electrical conductivity could be employed instead of or as well as the thermal coefficient of sound velocity.

As with previous examples an ANN correlation was trained, validated, and tested using the generated data of conductivity, sound velocity, and thermal coefficient of sound velocity. By using the trained ANN correlation, the PVCap concentration, EG concentration and salt concentration were simultaneously determined with an acceptable deviation. Results are shown in table 4 below, where Coefficient denotes the thermal coefficient of sound velocity ($\Delta V/\Delta T$), Exp denotes the actual (measured) concentration of the substance and ANN the concentration determined using the artificial neural network.

TABLE 4

Training and validation data for the EG-PVCap-NaCl systems

| T | Conductivity | Sound Velocity | Coefficient | NaCl, wt % | | PVCap wt % | | EG wt % | |
|---|---|---|---|---|---|---|---|---|---|
| ° C. | mS/cm | m/s | | Exp | ANN | Exp | ANN | Exp | ANN |
| 1.0 | 0.00457 | 1492.3 | 3.160 | 0.0 | 0.12 | 1.0 | 1.00 | 10.0 | 10.0 |
| 25.0 | 0.00750 | 1550.7 | 1.711 | 0.0 | 0.02 | 1.0 | 1.02 | 10.0 | 10.0 |
| 0.0 | 0.00130 | 1621.1 | 0.979 | 0.0 | 0.06 | 1.0 | 1.00 | 30.0 | 30.0 |

TABLE 4-continued

Training and validation data for the EG-PVCap-NaCl systems

| T | Conductivity | Sound Velocity | Coefficient | NaCl, wt % | | PVCap wt % | | EG wt % | |
|---|---|---|---|---|---|---|---|---|---|
| °C. | mS/cm | m/s | | Exp | ANN | Exp | ANN | Exp | ANN |
| 15.0 | 0.00258 | 1631.7 | 0.436 | 0.0 | −0.12 | 1.0 | 1.04 | 30.0 | 30.0 |
| 7.0 | 0.00470 | 1527.0 | 2.6196 | 0.0 | −0.03 | 2.0 | 2.02 | 10.0 | 10.0 |
| 24.0 | 0.00389 | 1644.7 | 0.214 | 0.0 | 0.15 | 2.0 | 1.87 | 30.0 | 30.0 |
| 0.0 | 17.24 | 1524.8 | 2.9339 | 3.0 | 2.90 | 1.0 | 1.03 | 10.0 | 10.0 |
| 16.0 | 26.95 | 1564.4 | 2.0187 | 3.0 | 3.01 | 1.0 | 1.03 | 10.0 | 10.0 |
| 23.0 | 16.62 | 1655.9 | 0.0783 | 3.0 | 2.95 | 1.0 | 0.98 | 30.0 | 30.0 |
| 6.0 | 18.95 | 1557.4 | 2.4479 | 3.0 | 2.95 | 2.0 | 2.04 | 10.0 | 10.0 |
| 2.0 | 7.88 | 1660.2 | 0.6666 | 3.0 | 2.99 | 2.0 | 1.97 | 30.0 | 30.0 |
| 19.0 | 13.49 | 1665.7 | −0.0270 | 3.0 | 3.00 | 2.0 | 1.98 | 30.0 | 30.0 |
| 1.0 | 6.44 | 1503.2 | 3.197 | 1.0 | 1.01 | 1.0 | 0.98 | 10.0 | 9.9 |
| 8.0 | 7.94 | 1524.0 | 2.731 | 1.0 | 1.00 | 1.0 | 0.98 | 10.0 | 10.0 |
| 25.0 | 12.16 | 1560.8 | 1.599 | 1.0 | 1.04 | 1.0 | 0.99 | 10.0 | 10.0 |
| 12.0 | 4.53 | 1637.8 | 0.6175 | 1.0 | 0.99 | 1.0 | 0.99 | 30.0 | 30.0 |
| 20.0 | 5.69 | 1642.3 | 0.5119 | 1.0 | 1.05 | 1.0 | 0.99 | 30.0 | 30.0 |
| 0.0 | 5.89 | 1519.8 | 2.9078 | 1.0 | 1.02 | 2.0 | 2.00 | 10.0 | 10.0 |
| 24.0 | 11.42 | 1573.9 | 1.6022 | 1.0 | 1.02 | 2.0 | 1.99 | 10.0 | 10.0 |
| 11.0 | 3.81 | 1651.4 | 0.2677 | 1.0 | 0.98 | 2.0 | 2.01 | 30.0 | 30.0 |
| 23.0 | 5.50 | 1652.6 | −0.0611 | 1.0 | 1.12 | 2.0 | 2.01 | 30.0 | 30.0 |
| 14.0 | 40.36 | 1584.2 | 2.006 | 5.0 | 5.06 | 1.0 | 0.99 | 10.0 | 10.0 |
| 4.0 | 28.09 | 1574.9 | 2.4111 | 5.0 | 4.98 | 2.0 | 2.00 | 10.0 | 10.0 |
| 22.0 | 45.43 | 1608.3 | 1.2987 | 5.0 | 4.99 | 2.0 | 2.01 | 10.0 | 10.0 |
| 3.0 | 14.06 | 1653.7 | 0.8344 | 4.58 | 4.62 | 0.94 | 0.99 | 28.3 | 28.4 |
| 10.0 | 17.71 | 1658.8 | 0.6118 | 4.58 | 4.63 | 0.94 | 0.99 | 28.3 | 28.3 |
| 6.0 | 14.03 | 1674.4 | 0.4261 | 4.77 | 4.76 | 1.94 | 1.98 | 29.1 | 29.1 |
| 24.0 | 23.93 | 1676.6 | −0.1787 | 4.77 | 4.58 | 1.94 | 1.95 | 29.1 | 29.0 |
| 0.0 | 13.63 | 1606.3 | 1.8724 | 3.75 | 3.74 | 1.6 | 1.46 | 20.0 | 20.0 |
| 25.0 | 28.19 | 1634.9 | 0.4124 | 3.75 | 3.78 | 1.6 | 1.47 | 20.0 | 20.0 |

Figure 7:
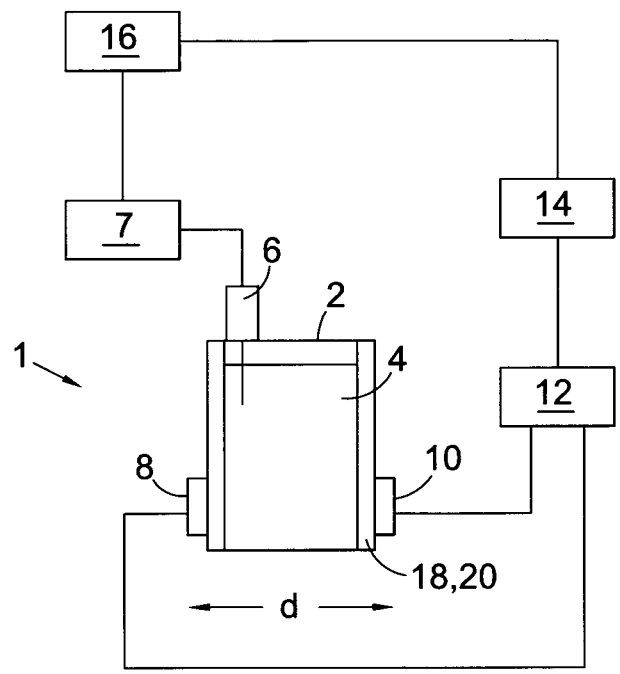
FIG. 7 shows schematically an apparatus of the invention for determination of conductivity and sound velocity of fluid samples.

FIG. 7 shows an apparatus for carrying out the methods of the invention in a laboratory. The apparatus 1 has a pressurisable sample cell 2 for fluid samples 4. An electrical conductivity sensor 6 and associated meter 7 is connected to the cell for measuring electrical conductivity of the sample 4 under test. Two ultrasonic transducers 8, 10 are connected to a Transmitter/Receiver 12. The Transmitter/Receiver generates an electrical pulse and sends it to one of the two transducers 8, 10. The transducer converts the electrical pulse signal into an ultrasonic signal passing through the sample. The other transducer acting as a sound receiver converts the ultrasonic signal into electrical signal and sends it back to the Transmitter/Receiver 12. The received signal is pre-amplified and then sent to a digital oscilloscope 14. The digital oscilloscope 14 shows the waveforms and saves the waveform data to a personal computer 16. The sound velocity is determined by the known distance d between the two transducers 8, 10 divided by the measured time a pulse takes to travel between the two transducers.

The sample cell in this example is equipped with a cooling jacket 18 surrounded with a thermal insulation layer 20. This allows the temperature of the system to be maintained or altered as required, depending on the test regime being implemented. The temperature may conveniently be measured by making use of a conductivity sensor 6 that incorporates a temperature measuring capability. Alternatively a separate thermometer (not shown) may be employed. The personal computer 16, which receives the output from the conductivity meter 7 as well as from the oscilloscope 14, is equipped with the appropriate software to carry out artificial neural network training/validation and to then evaluate test samples with unknown analyte concentrations.

Figure 8:
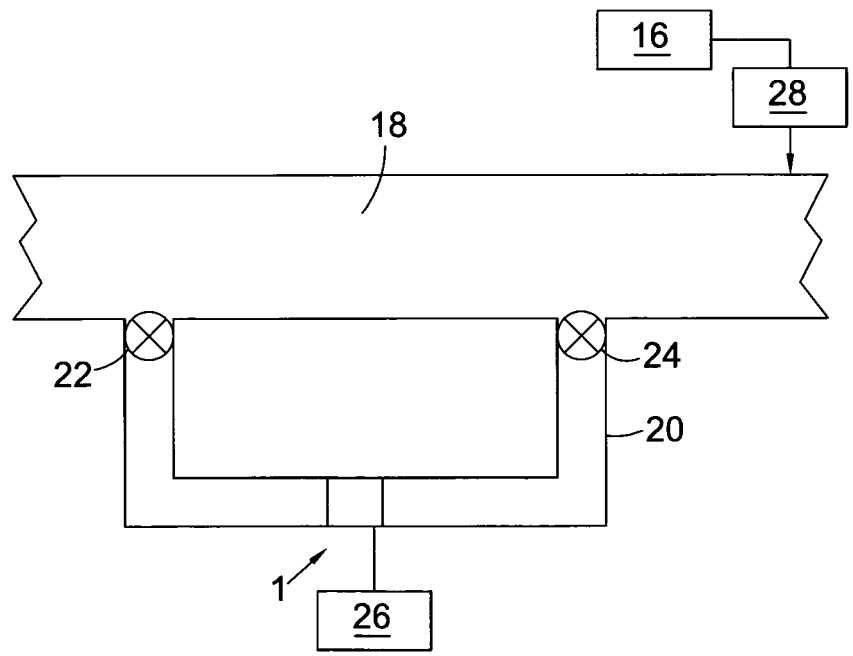
FIG. 8 shows schematically another apparatus of the invention for on-line analysis.

FIG. 8 shows schematically the use of an on-line apparatus 1 of the invention on a sub-sea pipeline 18. The apparatus 1 is fitted in a by-pass loop 20 fitted at a low point of the pipeline 18 so that for example produced water can be drained into the by-pass loop 20 via the remotely operable valves 22,24 when testing is desired. The apparatus 1 is fitted with a conductivity sensor, sonic transducers and a transmitter/receiver similar to those described above for FIG. 7. (Not shown in this figure for clarity). Temperature may be measured by use of a conductivity sensor incorporating temperature measuring capability or by means of a separate temperature sensor. The apparatus 1 communicates by wireless link 26 to a suitable computer 16 at the surface which analyses results of pressure, temperature, sound velocity and conductivity measurements and determines the concentration of hydrate inhibitors and hence the hydrate safety margin of the system. The results obtained can be used for automatic adjustment of hydrate inhibitor concentration by means of a dosing system 28, which feeds inhibitors into the pipeline 18.

A skilled person will appreciate that variations of the disclosed arrangements are possible without departing from the invention. Accordingly the above description of a specific embodiment is made by way of example only and not for the purposes of limitation. It will be clear to the skilled person that minor modifications may be made without significant changes to the operation described.

REFERENCES

1. Clay, C. S. and Medwin, H. 1977. Acoustic Oceanography: Principles and Application, New York, Wiley
2. Jerie, K., Baranowski A., Przybylski J, and Glinski J. 2004. Electrolytic solutions in ethylene glycol: ultrasonic and positron annihilation studies. *Physics Letters A* 323: 148-153.
3. Vibhu, I., Singh, A. K, Gupta, M. and Shukla, J. P. 2004. Ultrasonic and IR investigation of N—H—N complexes in ternary mixtures. *Journal of Molecular Liquids* 115: 1-3.

4. Goodenough, T. I. J., Rajendram, V. S., Meyer, S. and Pretre D. 2005. Detection and qualification of insoluble particles by ultrasound spectroscopy. *Ultrasonics* 43: 231-235.
5. Vyas, J. C., Katti, V. R., Gupta, S. K. and Yakhmi, J. V. 2006. A non-invasive ultrasonic gas sensor for binary gas mixtures. *Sensors and Actuators B* 115: 28-32.

The invention claimed is:

1. A method for determining concentration of constituents of an aqueous phase, the aqueous phase being one of from a petroleum related system and in a petroleum related system, the method comprising:
   measuring a plurality of different properties of the aqueous phase, the plurality of different properties being at least same in number as a number of plural constituents of unknown concentrations comprised in the aqueous phase, the plurality of different properties varying differently from each other in dependence on variation in concentration in the aqueous phase of each of the plural constituents, the plurality of different properties being selected from a group consisting of: electrical conductivity, sound velocity, rate of change of sound velocity with temperature, and rate of change of electrical conductivity with temperature; and
   determining the concentration in the aqueous phase of at least one of the plural constituents by applying the measurements of the plurality of different properties of the aqueous phase to a model of predetermined relationships between the plurality of different properties and concentrations of the plural constituents which characterize how the plurality of different properties vary differently from each other in dependence on variation in concentration in the aqueous phase of each of the plural constituents.

2. A method according to claim 1 wherein the different properties measured are the sound velocity and the electrical conductivity.

3. A method according to claim 1 wherein the sound velocity is measured and the sound measured is ultrasound.

4. A method according to claim 1 further comprising using the determined concentration of the at least one of the plural constituents to determine a safety margin for at least one constituent of the aqueous phase.

5. A method according to claim 4 wherein the constituents of the aqueous phase whose concentration is determined is a hydrate inhibitor and the determined concentration is used to determine a safety margin for the hydrate inhibitor which provides a hydrate safety margin in the aqueous phase.

6. A method according to claim 1 wherein concentrations of two constituents of the aqueous phase are determined.

7. A method according to claim 1 wherein the constituents of the aqueous phase comprise a salt and one of: an organic hydrate inhibitor; and a low dosage hydrate inhibitor, and concentrations of said constituents are determined for the aqueous phase.

8. A method according to claim 1 wherein the constituents of the aqueous phase comprise a salt, an organic hydrate inhibitor and a low dosage hydrate inhibitor and concentrations of said constituents are determined by measuring the sound velocity; the electrical conductivity; and one of the rate of change of sound velocity with temperature and rate of change of electrical conductivity with temperature.

9. A method according to claim 1 wherein an on-line sampling method is used.

10. A method for controlling the concentration of constituents of an aqueous phase in a petroleum related system, the method comprising:
    determining the concentration in the aqueous phase of at least one of the plural constituents of the aqueous phase by the method of claim 1; and
    adjusting in the petroleum related system the concentration of at least one of the plural constituents in the aqueous phase depending on the determined at least one concentration in the aqueous phase.

11. A method according to claim 10 wherein the adjustment in the petroleum related system of the concentration of the at least one of the plural constituents of the aqueous phase is carried out automatically in dependence on the measurement of the plurality of different properties of the aqueous phase when the aqueous phase is in a petroleum related system.

12. A computer program product comprising computer readable instructions stored on a non-transitory computer readable medium that are executable to determine concentration of constituents of an aqueous phase, the aqueous phase being one of from a petroleum related system and in a petroleum related system, said computer readable medium comprising:
    an executable portion configured to measure a plurality of different properties of the aqueous phase, the plurality of different properties being at least same in number as a number of plural constituents of unknown concentrations comprised in the aqueous phase, the plurality of different properties varying differently from each other in dependence on variation in concentration in the aqueous phase of each of the plural constituents, the plurality of different properties being selected from a group consisting of: electrical conductivity, sound velocity, rate of change of sound velocity with temperature, and rate of change of electrical conductivity with temperature;
    a model of predetermined relationships between the plurality of different properties and concentrations of the plural constituents which characterize how the plurality of different properties vary differently from each other in dependence on variation in concentration in the aqueous phase of each of the plural constituents; and
    an executable portion configured to determine the concentration in the aqueous phase of at least one of the plural constituents by applying the measurements of the plurality of different properties of the aqueous phase to the model.

13. A method according to claim 1 comprising: measuring at least two of: the electrical conductivity of the aqueous phase; the sound velocity in the aqueous phase; temperature of the aqueous phase; and determining the concentration in the aqueous phase of the at least one of the plural constituents in the aqueous phase in dependence on said measurements.

14. A method according to claim 1 wherein the model is an artificial neural network, the method further comprising: measuring a plurality of different properties of at least one test fluid comprising known concentrations of the plural constituents comprised in the aqueous phase, the plurality of different properties of the at least one test fluid corresponding to the plurality of different properties of the aqueous phase; and training the artificial neural network by applying the measurements of the plurality of different properties of the at least one test fluid and the known concentrations of the plural constituents to the artificial neural network.

15. A method according to claim 1 wherein the aqueous phase for which the plurality of different properties are measured is one of from a hydrocarbon pipeline and in a hydrocarbon pipeline, the hydrocarbon pipeline being comprised in the petroleum related system.

* * * * *